United States Patent [19]

Galindo

[11] Patent Number: 5,665,108
[45] Date of Patent: Sep. 9, 1997

[54] SURGICAL DRESSING STRAP

[76] Inventor: Eugene R. Galindo, 11527 Orcas Ave., Lake View Terrace, Calif. 91342

[21] Appl. No.: 714,575

[22] Filed: Sep. 16, 1996

[51] Int. Cl.$^6$ .................................................. A61B 17/08
[52] U.S. Cl. ....................................... 606/215; 606/41
[58] Field of Search .................................. 606/213–216; 602/41, 42

[56] References Cited

U.S. PATENT DOCUMENTS

| | | | |
|---|---|---|---|
| 345,541 | 7/1886 | Reichardt | 606/216 |
| 1,774,489 | 10/1930 | Sarason | 606/216 |
| 1,969,188 | 8/1934 | Spicer | 606/216 |
| 5,234,462 | 8/1993 | Pavletic | 606/215 |
| 5,534,010 | 7/1996 | Peterson | 606/215 |

Primary Examiner—Michael Buiz
Assistant Examiner—Tina T. D. Pham
Attorney, Agent, or Firm—Linval B. Castle

[57] ABSTRACT

A dressing strap for securing a dressing to a patient's skin comprises a pad of plastic topped gelatin-like hydrocolloid with an overlay flap which covers a surgical dressing and which supports a plurality of resilient plastic hooks that may be quickly laced with either string of elastic bands. The overlay flap is attached to the hydrocolloid plastic cover near its centerline, thus eliminating stress at the wound.

7 Claims, 3 Drawing Sheets

SURGICAL DRESSING STRAP

This invention relates in general to surgical appliances and in particular to a novel dressing strap for securing surgical dressings.

BRIEF SUMMARY OF THE INVENTION

Various types of appliances for holding surgical dressings in place have been availainable for many years. Dressing straps and adhesive devices for drawing together the edges of a wound have advanced the art up to the use of adhesive coated Velcro pads (U.S. Pat. No. 5,234,462) and the popular and well-known Montgomery strap.

The Montgonery strap comprising a satin material about seven inches wide, five inches of which are adhesive coated on one surface. It is normally twelve inches long with a row of ¼ inch holes along the non-adhesive edge, and may be cut to a desired length. In use, a Montgomery strap is applied to the skin at least three inches each side of the wound and a string is laced through the holes to draw the wound edges together and to hold a pad or gauze sponge against the wound. The problem was not only the time required to apply and remove the dressing but very often the shear tension of the satin adhesive pulling on the skin caused skin irritation and blistering of the skin. This could have been avoided by placing a skin barrier pad, such as a hydrocolloid, which does not cause the irritation of normal adhesives, under the adhesive of the Montgomery strap.

The dressing strap of this invention uses flat plastic hooks that are welded to a plastic overlay panel that is attached near the center of a hydrocolloid pad which adheres to the skin but may be readily removed without the use of solvents. There is virtually no skin sensitivity to hydrocolloid and the fact that the overlay panel is welded near the center of the hydrocolloid barrier pad eliminates stress at the edges of the wound. A string or elastic bands may be quickly laced on the plastic hooks to ease together the edges of the wound.

BRIEF DESCRIPTION OF THE DRAWINGS

In the drawings which illustrate the preferred embodiment of the invention.

DETAILED DESCRIPTION

Figure 1:
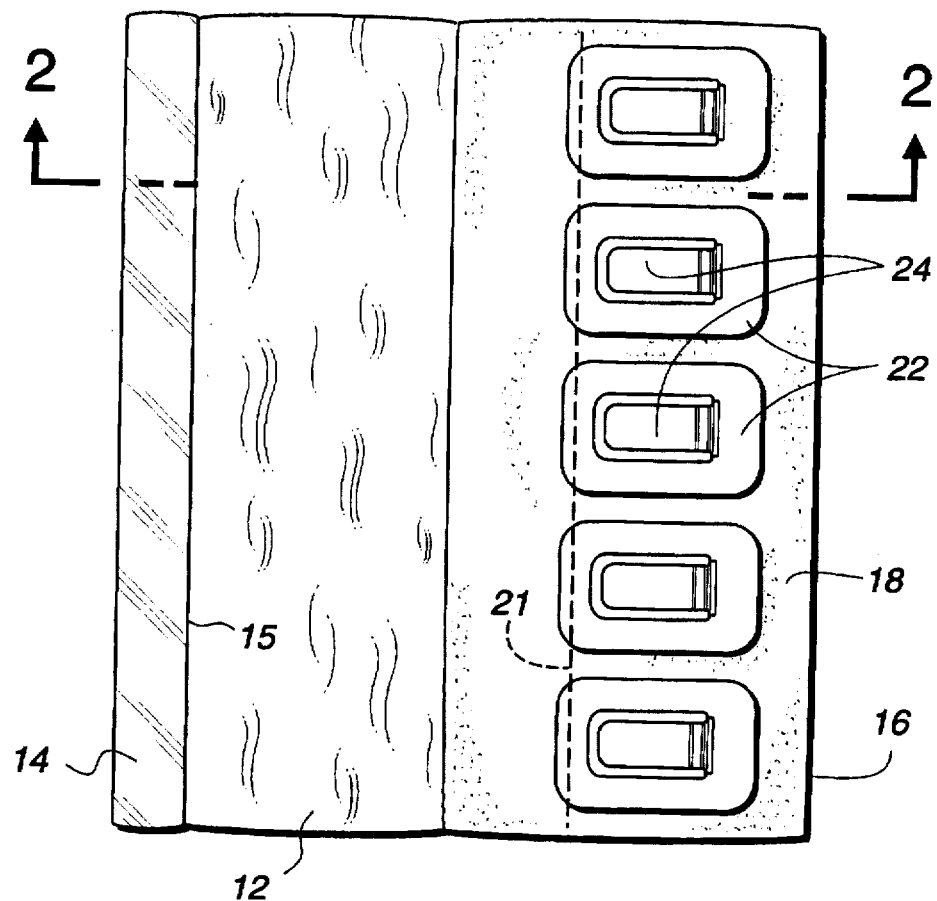
FIG. 1 is a plan view illustrating the dressing strap of the invention.
Figure 2:
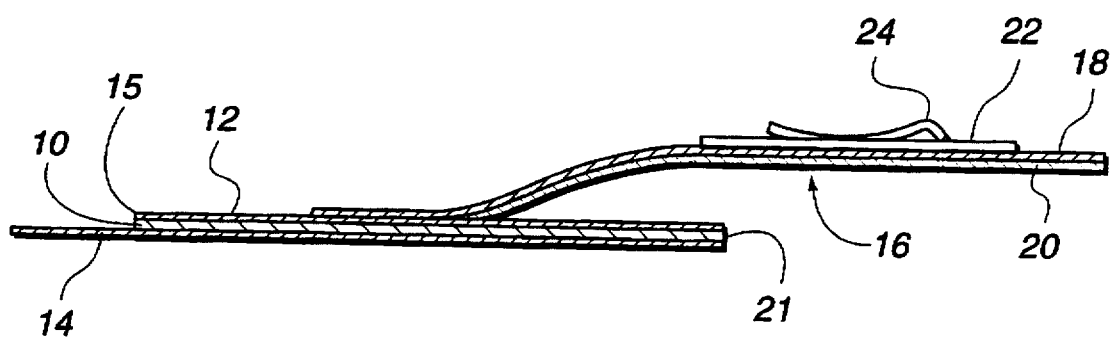
FIG. 2 is an edge view taken along the lines 2—2 of FIG. 1.

The dressing strap is illustrated in the plan view of FIG. 1 and in the edge view of FIG. 2. Instead of a pressure sensitive adhesive to bond to the skin of the patient, the strap uses a pad 10 of a thin gelatin-like hydrocolloid material to which there is virtually no skin sensitivity and which is easily removed without solvents. A thin plastic barrier cover 12, such as Mylar, is welded to the top surface and a silicone treated glazed peel-off paper 14 is applied over the bottom surface as temporary covering. The overall size of the hydrocolloid pad 10 is approximately ¹⁄₁₆ inch thick, 3½ wide and, in the plan view of FIG. 1, 6 inches long.

Welded to the plastic barrier cover 12 approximately 2¼ inches from the left edge 15 is the edge of an overlay panel 16 comprising a plastic sheet 18, such as Mylar, with a soft, non-woven fiber sheet 20 welded to the lower surface to separate the plastic sheet 18 from the wound dressing. The overlay panel 16 is about 3 inches wide and is as long as the hydrocolloid pad 10 and its plastic barrier cover 12, and its left edge attachment 2¼ inches from the left edge of the barrier cover 12 results in its right edge extending 1¾ inches past the the straight right edge 21 of the hydrocolloid pad 10 which is shown by a broken line 21 in FIG. 1.

The advantage of attaching the overlay panel 16 near the centerline of the barrier cover 12 is to prevent stress on the edges of the wound. With the tension of the overlay panel near the center of the barrier cover, stresses at the edge of wound under the dressing are minimal.

Welded to the top surface of the plastic sheet 18 of the overlay panel 16 are the frames 22 of plastic hooks 24. The frames 22 are each 1 inch×1½ inch and rectangular in shape, they are separated from each other ¼ inch and are in a row that is set back from the right edge of the overlay panel 16 by ⅜ inch. Each frame 22 contains a central rectangular shaped resilient plastic hook 24 which is ¾ inches long and ⅜ inches wide which is attached to its respective frame at one end and which is low so that it doesn't protrude excesively but is slightly curved up at the ends as shown in FIG. 2 so that a string or elastic band may be easily attached to the hook.

Figure 3:
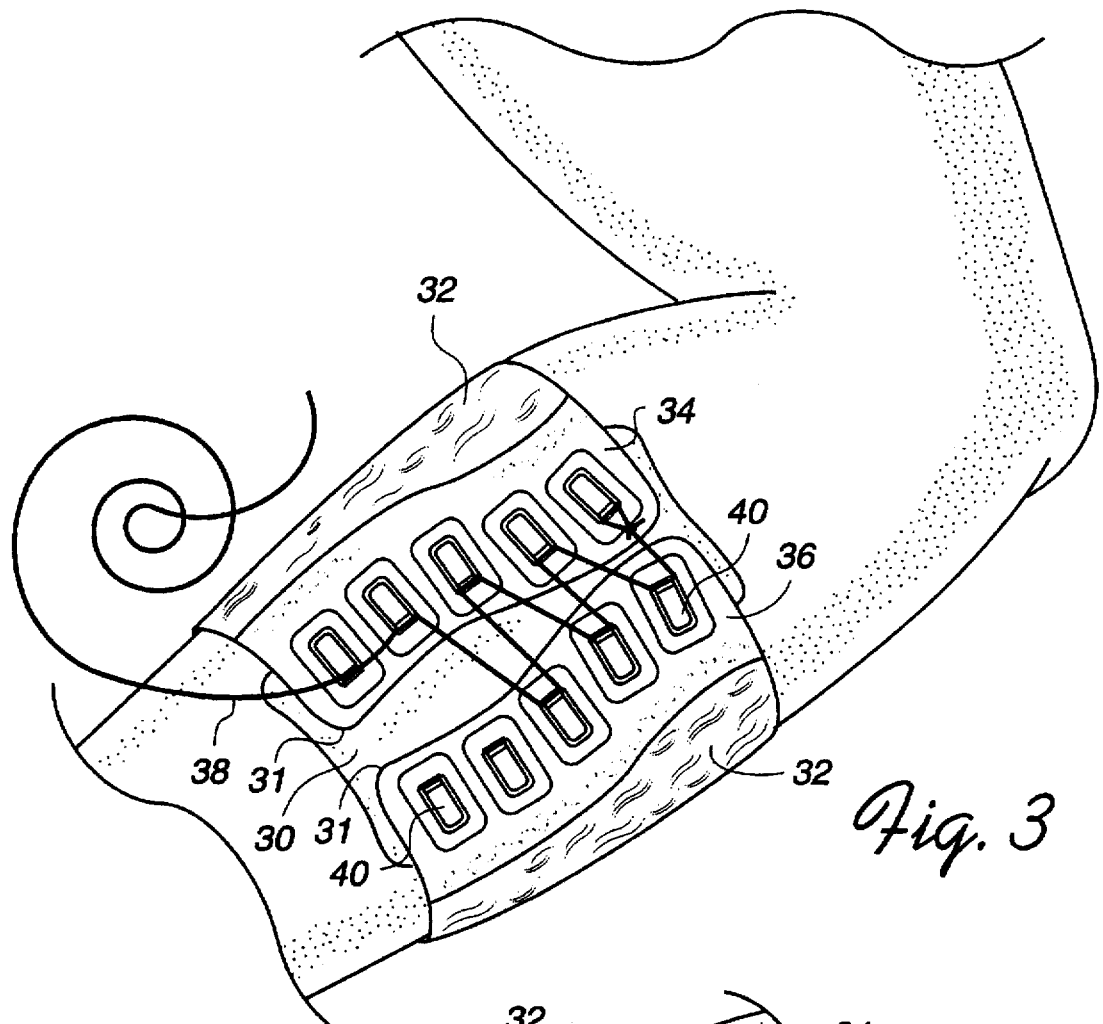
FIG. 3 illustrates the application of dressing straps to a dressing on a limb wound.
Figure 4:
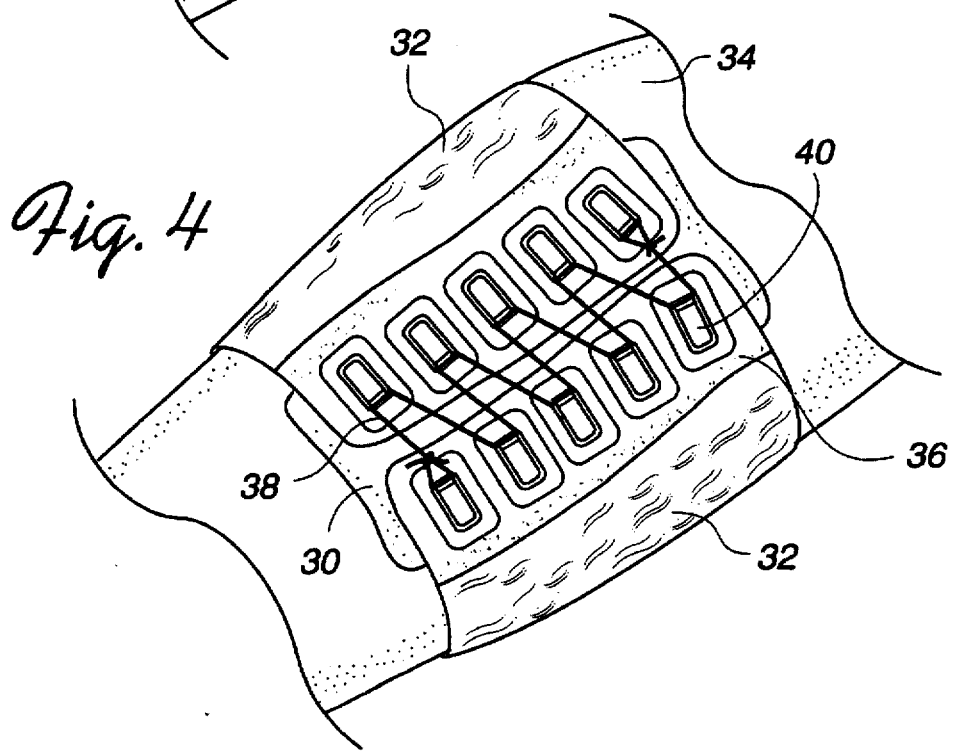
FIG. 4 illustrates the completed dressing of FIG. 3 using a string lacing.

FIG. 3 is a view illustrating the application of a dressing strap to a dressing 30 on an arm. Two lengths of long dressing strap are cut into appropriate lengths and the peel-off paper backing is removed from bottom surfaces of the hydrocolliod pad 32. The straps are positioned on each side of the dressing 30 so that the edges 31 of the overlay panels 34 and 36 each face the dressing and are spaced approximately one inch. Note that the closest either hydrocolloid pad edge is to the dressing is about 2 inches thereby leaving adequate space for additional dressings that may be held under the overlay panels 34,36. Once the hydrocolloid pad 32 is properly positioned, a string 38 may be easily and quickly laced through the several hooks 40 and tightened, as shown in FIG. 4, to secure the dressing 30 and possibly to draw together the edges of the wound.

Figure 5:
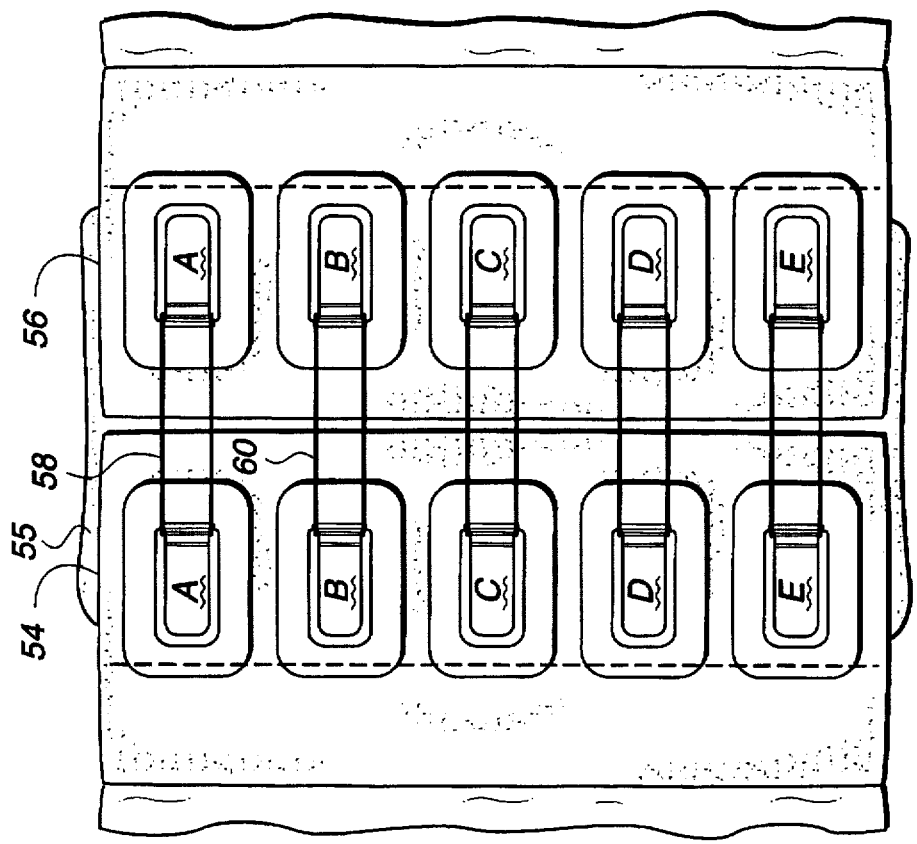
FIG. 5 illustrates the used of rubber bands for lacing the plastic hooks on an abdominal dressing strap.

FIG. 5 illustrates the lacing of two dressing straps 42,44 securing an abdominal dressing pad 45 using eight elastic bands coupled to the five hooks on each strap. The bands are coupled in a cross pattern with two bands forming an "X". Thus the band 46 is connected to the hook "A" on strap 42 and to hook "B" on strap 44, and elastic band 48 is connected to hook "A" on strap 44 and to hook "B" on strap 42. Similarly, elastic band 50 is connected to the strap 42, hook "B" and to strap 44, hook "C", and band 52 is connected to strap 44, hook "B" and to strap 42, hook "C". This "X" pattern of elastic band lacing provides a firm but resilient closure.

Figure 6:
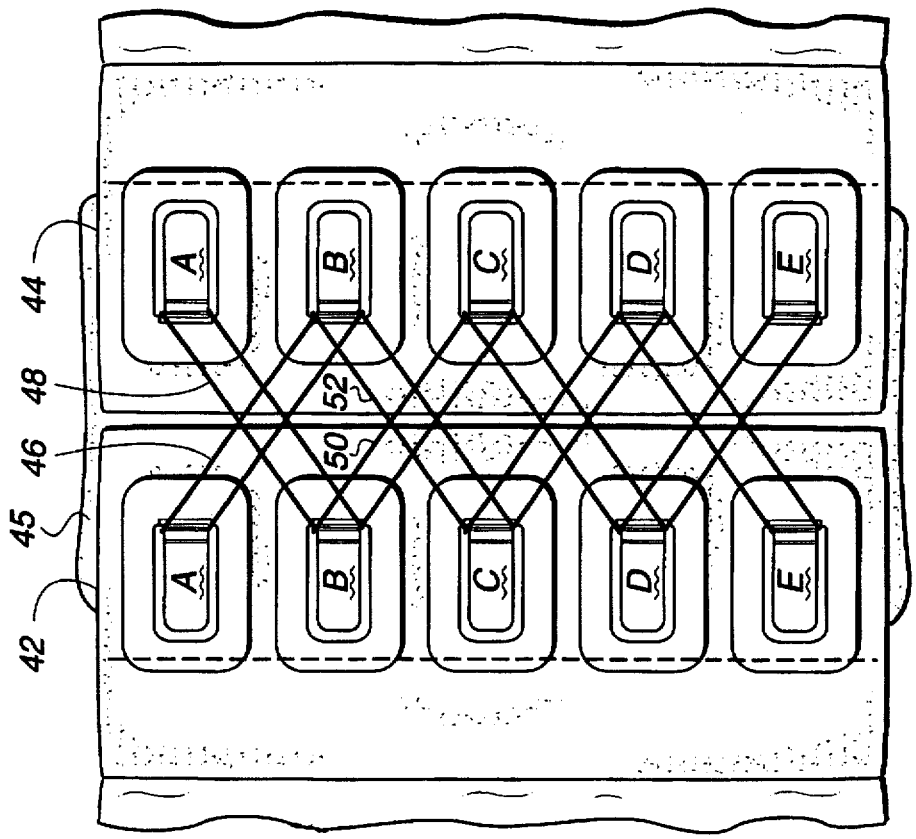
FIG. 6 illustrates an alternate use of rubber band for lacing on the plastic hooks of an abdominal dressing strap.

FIG. 6 illustrates a similar dressing strap using a simple cross-lacing for securing an abdominal dressing pad 55 in which four elastic bands are connected to four corresponding hooks. Thus, elastic band 58 is connected to hooks "A" on both dressing straps 54 and 56; and band 60 is connected to hooks "B" on both straps.

The use of elastic bands for lacing together the dressing straps provides a firm but resilient closure of the straps and provides a fast and efficient method of applying and changing a dressing.

I claim:

1. A dressing strap comprising;

a thin hydrocolloid pad having at least one straight edge, said pad having a top and a bottom surface;

a plastic barrier cover on said top surface;

a rectangular overlay sheet having top and bottom surfaces, a first edge of said overlay sheet attached to said barrier cover along a line parallel with said straight edge but displaced from said straight edge; and a plurality of flexible hooks aligned on the top surface of said overlay sheet along a line parallel with said straight edge, said hooks being formed of a thin resilient rectangular plastic that is slightly curved up at each end, one end of each of said plurality of hooks being connected to a frame portion that is welded to said overlay sheet.

2. The dressing strap claimed in claim 1 further including a glazed peel-off sheet temporarily attached to the bottom surface of said hydrocolloid pad.

3. The dressing strap claimed in claim 1 further including a sheet of non-woven fiber adhering to the bottom surface of said overlay sheet.

4. A method for securing a surgical dressing to the skin of a patient, said method comprising the steps of:

applying identical dressing straps to the patient's skin spaced from each side of the dressing, each of said dressing straps comprising a hydrocolloid pad having a plastic barrier cover on the top surface thereof, an overlay sheet having an edge attached to said barrier cover near the center thereof, and at least one plastic frame welded to said overlay sheet, said frame having a central resilient hook that is free of the weld on said frame;

lacing together said resilient hooks on said identical dressing straps.

5. The method claimed in claim 4 wherein said step of lacing is done with elastic bands engaging corresponding hooks on said straps.

6. The method claimed in claim 5 wherein each overlay sheet on each dressing strap has a plurality of hooks, and said step of lacing is done with elastic bands forming an "X" pattern between the hooks on said dressing straps.

7. The method claimed in claim 4 wherein said step of lacing will draw together edges of a wound under said surgical dressing.

* * * * *